(12) United States Patent
Loyd et al.

(10) Patent No.: US 9,808,478 B2
(45) Date of Patent: Nov. 7, 2017

(54) CONTROL RELEASE OF FAT SOLUBLE ANTIOXIDANTS FROM AN ORAL FORMULATION AND METHOD

(71) Applicants: Steven Loyd, Lynnwood, WA (US); George Blouin, Seattle, WA (US); Newsha Farahani, Issaquah, WA (US); Robert Burns, Seattle, WA (US)

(72) Inventors: Steven Loyd, Lynnwood, WA (US); George Blouin, Seattle, WA (US); Newsha Farahani, Issaquah, WA (US); Robert Burns, Seattle, WA (US)

( * ) Notice: Subject to any disclaimer, the term of this patent is extended or adjusted under 35 U.S.C. 154(b) by 0 days.

(21) Appl. No.: 15/131,888

(22) Filed: Apr. 18, 2016

(65) Prior Publication Data

US 2017/0020908 A1    Jan. 26, 2017

Related U.S. Application Data

(60) Provisional application No. 62/149,063, filed on Apr. 17, 2015.

(51) Int. Cl.
| | | |
|---|---|---|
| A61K 9/50 | (2006.01) | |
| A61K 31/7048 | (2006.01) | |
| A61K 9/00 | (2006.01) | |
| A61K 31/353 | (2006.01) | |
| A61K 45/06 | (2006.01) | |

(52) U.S. Cl.
CPC ........ *A61K 31/7048* (2013.01); *A61K 9/0019* (2013.01); *A61K 9/0053* (2013.01); *A61K 9/501* (2013.01); *A61K 9/5047* (2013.01); *A61K 9/5078* (2013.01); *A61K 9/5089* (2013.01); *A61K 31/353* (2013.01); *A61K 45/06* (2013.01)

(58) Field of Classification Search
CPC .... A61K 2300/00; A61K 33/00; A61K 33/08; A61K 33/10; A61K 31/122; A61K 31/592; A61K 31/7016; A61K 33/42; A61K 9/5047; A61K 9/0019; A61K 9/10; A61K 9/501; A61K 31/00; A61K 31/353; A61K 31/704
See application file for complete search history.

(56) References Cited

U.S. PATENT DOCUMENTS

2007/0218126 A1 *  9/2007  Gurol .................. A61K 9/0014
                                                               424/458
2007/0275060 A1 * 11/2007  Befumo .............. A61K 9/2009
                                                               424/468

FOREIGN PATENT DOCUMENTS

IT          WO99/17745       *  4/1999  ............... A61K 9/20

OTHER PUBLICATIONS

"68040-610: Vasculera (Diosmin 600 Mg/ Calcium magnesium potassium carbonate chloride hydroxide 30 mg)", Medschat.com, The People's Medicine Community TM. Accessed online Jun. 11, 2017.*
"Vasculera—diosmiplex 630 mg", revised Apr. 2012 and accessed Jun. 11, 2017. https://dailymed.nim.niih.gov/dailymed/fda/fdaDrugxsl.cfm?setid=563d3d34-a547-471e-aecd-f4a4a57cbf1d.*

* cited by examiner

*Primary Examiner* — Audrea Buckley
(74) *Attorney, Agent, or Firm* — Dean A Craine

(57) ABSTRACT

Oral formulation of particles made of an agglomeration of a plurality of seed granules or a single seed granule both surrounded by three layers and an outer gel coating. The seed granules are made of calcium carbonate with microscopic fissures. Disposed inside the fissures and in the interstitial spaces of the agglomerate seed granules are microscopic particles of alkali metal salts and other ions. Coating the agglomerate or single seed granules is an alkaline-resistant first layer made of microcrystalline cellulose and croscarmellose sodium that binds and protects the surrounding second layer. Surrounding the second layer is a third layer made of alkaline earth metal salt particles holding alkali metal hydroxide ions within a polysaccharide or polymer gel. Surrounding the third layer is at least one outer gel layer. The fourth and third layers dissolve in a low pH environment and release the fat soluble antioxidant and ions in the seed granule fissures.

9 Claims, 7 Drawing Sheets

CONTROL RELEASE OF FAT SOLUBLE ANTIOXIDANTS FROM AN ORAL FORMULATION AND METHOD

This utility patent application is based on and claims the filing date benefit of U.S. provisional patent application (62/149,063) filed on Apr. 17, 2015.

Notice is given that the following patent document contains original material subject to copyright protection. The copyright owner has no objection to the facsimile or digital download reproduction of all or part of the patent document, but otherwise reserves all copyrights.

BACKGROUND OF THE INVENTION

1. Field of the Invention

The present invention relates to control release of ingredients in oral formulations and more particularly to the control release of fat soluble antioxidants including but not limited to flavonoids in oral formulations.

2. Description of the Related Art

Fat soluble antioxidants are defined here as phenolic or polyphenolic phytochemicals with low solubility in water and neutralize oxygen free radicals in vitro. They include vitamin E, ellagic acid, curcumin, capsaicin and the flavonoid family of compounds. Flavonoids are a class of plant metabolites with a general structure of a 15-carbon skeleton, which comprises two phenyl rings and a heterocyclic ring. The present invention includes phytonutrient flavonoids and certain derivatives having a general structure of a 14- to 30-carbon skeleton, which comprises two phenyl rings (referred to as "fat soluble antioxidants" or "FSA").

Fat soluble antioxidants are part of the human diet and are found ubiquitously in plants. Their wide distribution, variety and low toxicity mean that many animals, including humans, ingest significant quantities in their diet. Dietary sources of fat soluble antioxidants, such as flavonoids are well documented.

In vitro studies have shown flavonoids to have a wide range of biological and pharmacological activities. Examples include anti-inflammatory, antioxidant, capillary vein rebuilding, antimicrobial and antiviral activities.

Flavonoids are effective scavengers of free radicals in the test tube (in vitro) and an excellent scavenger of most Reactive Oxygen Species ("ROS"). With their level of reactivity, not surprisingly, flavonoids degrade when exposed to light and oxygen during storage and cooking, and degrade with enzymes and acids during digestion.

Flavonoids are fat soluble and are insoluble in water. Absorption in the GI tract is low as is flavonoid bioavailability. New formulations of flavonoid delivery systems focus on biocompatible organic substances like liposomes, polyethylene glycols, biopolymers, cellulose, corn oil and hydrogels chemically attached to the flavonoid.

Other attempts to improve flavonoid absorption involve attaching flavonoid to lipids, liposomes, albumins, cyclodextrin, cucurbituryl, surfactants, and natural and synthetic polymers.

Research at the Linus Pauling Institute and the European Food Safety Authority shows that flavonoids are poorly absorbed in the human body (less than 5%), with most of what is absorbed being metabolized and excreted.

There is, accordingly, an ongoing need in the art for a general delivery formulation that allows, fat soluble anti-oxidants, such as flavonoids, to survive storage and digestive processes until the fat soluble anti-oxidant can be released in full potency when the desired pharmacokinetic conditions are present (typically in the upper intestinal tract) and to coincidentally release molecules in the GI tract to aid in the absorption of the fat soluble antioxidant across the intestinal lumen and villi.

An ideal formulation would protect the fat soluble antioxidant from light, air, abrasion or chemical interaction under normal conditions; extend shelf-life for fat soluble antioxidant based products; and protect the fat soluble antioxidant for up to twenty (20) minutes after ingestion so the fat soluble antioxidant safely passes through the highly acidic, enzyme-active stomach intact; and releases the fat soluble antioxidant directly into the gut coincidentally with molecules to aid in flavonoid absorption through the lumen mucous membrane and villi to pass into the blood stream or into the lymphatic system.

SUMMARY OF THE INVENTION

A controlled release oral formulation containing a fat soluble antioxidant layer containing one or more fat soluble antioxidants (hereinafter aka "FSA"). The oral formulation is made of two types of particles. One particle made up on a plurality of seed granules (called a seed granule agglomerate and known as a Type 1 seed granule) bound together and the other particle made up of a single seed granule, (known as a Type 2 seed granule). The seed granules are made of microscopic (0.5 µm to 20 µm) alkaline earth metal crystal and include microscopic fissures formed therein Disposed inside the microscopic fissures are microscopic particles of alkali metal salt, alkali metal hydroxide or other ions. Disposed in the interstitial spaces between the seed granules in the Type 1 particles are also microscopic particles of alkali metal salt, alkali metal hydroxide and other ions.

Coating the seed granule agglomerate and the single seed granule is a first layer made of microcrystalline cellulose ("MCC") and/or croscarmellose sodium that is alkaline-resistant and binds to the seed granule. Surrounding the first layer is a second layer made of a fat soluble antioxidant mixture. The first layer separates the highly reactive seed granules from a surrounding second layer made of a fat soluble antioxidant mixture.

Surrounding the FSA second layer is a third layer made of microscopic alkaline earth metal salt particles in a mixture holding microscopic alkali metal hydroxide ions in fissures and interstitial spaces within polysaccharide or polymer gel. The third layer is configured to protect the fat soluble antioxidant in the second layer from the atmosphere and light and protect the fat soluble antioxidant from enzymes and acids in the stomach for a period of 20 to 30 minutes. Surrounding the third layer is at least one outer layer made of hardened, thermo-sensitive polymer gel, (preferably hydroxypropyl methylcellulose aka "HPMC").

When the particles are exposed to a low pH environment in the stomach, the third and fourth layers slowly dissolve. The second layer made of fat soluble antioxidant mixture is exposed. When the particles pass into the small intestine with a high pH environment, the second layer and then the first layers sequentially disperse and dissolve releasing the fat soluble antioxidant and the ions in the interstitial spaces and fissures of the seed granules. It is postulated that ions in the seed granules are released to open ion channels in the small intestine allowing more fat soluble antioxidant to be absorbed.

DESCRIPTION OF THE PREFERRED EMBODIMENT(S)

I. Definitions and Nomenclature

Figure 1:
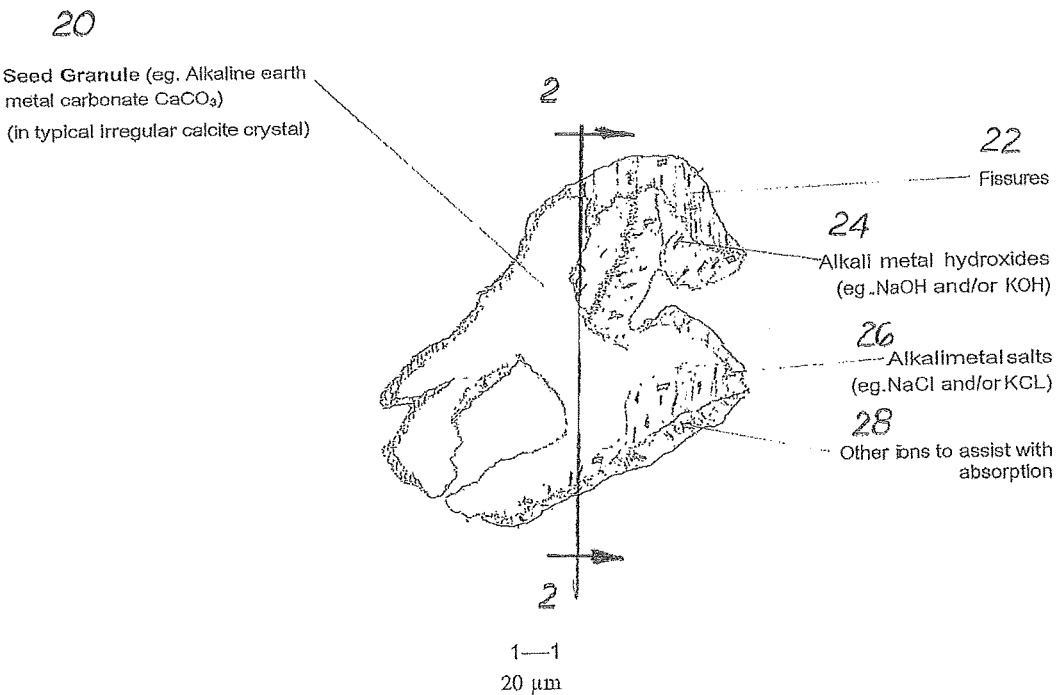
FIG. 1 is an illustration of a Type 1 seed granule made of a plurality of microscopic alkaline earth metal carbonate crystals with interstitial spaces and fissures.
Figure 2:
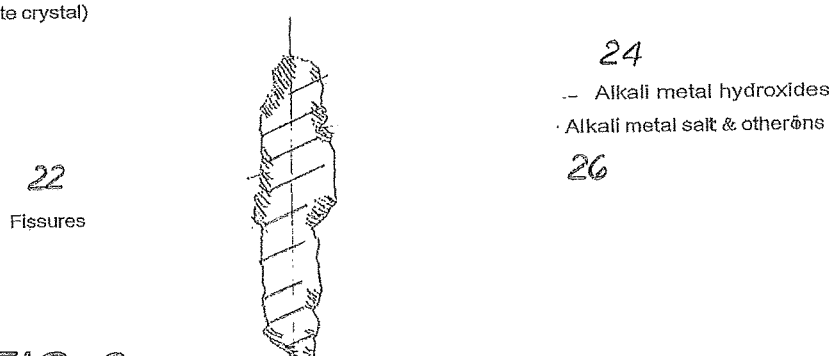
FIG. 2 is an illustration of an irregular shaped Type 2 seed granule made of a single alkaline earth metal carbonate with a plurality of fissures.
Figure 3:
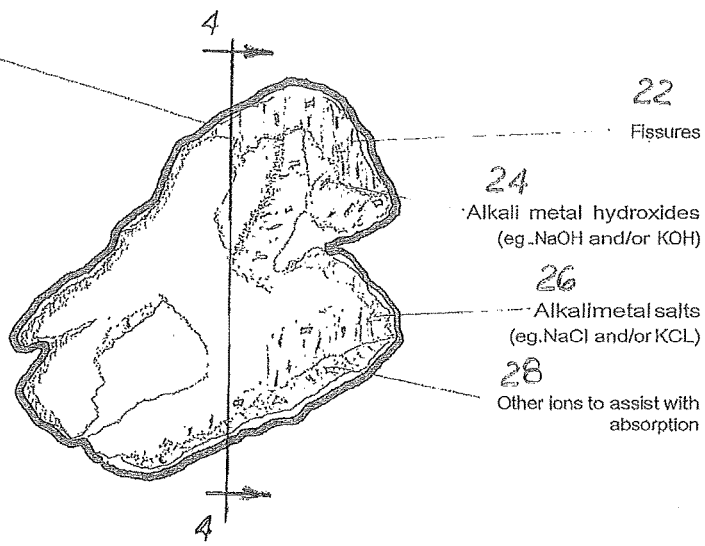
FIG. 3 is a sectional, side elevational view of the seed granule shown in FIG. 2.
Figure 4:
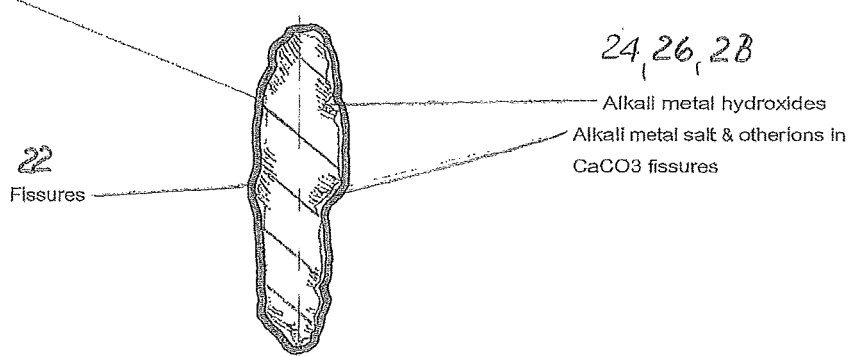
FIG. 4 is an illustration showing the first layer containing MCC surrounding the seed granule.
Figure 5:
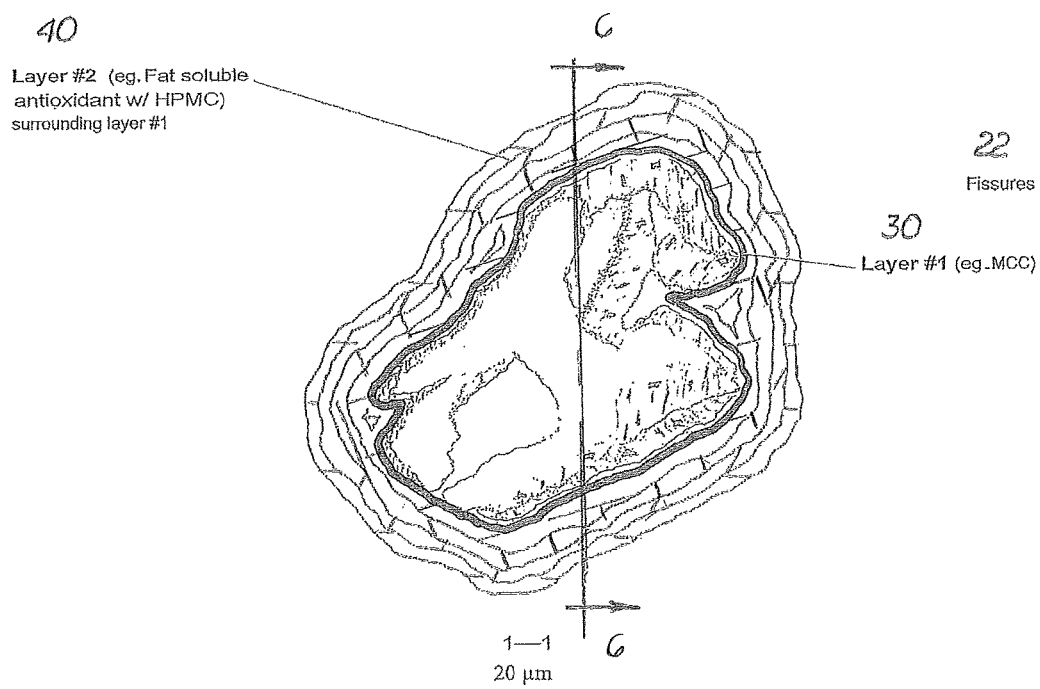
FIG. 5 is a sectional, side elevational view of the seed granule covered by the first layer as shown in FIG. 4.
Figure 6:
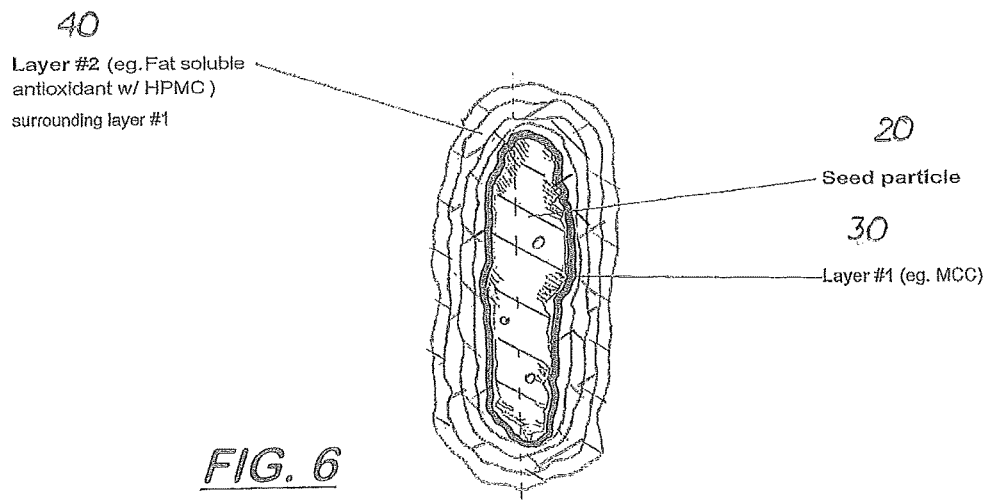
FIG. 6 is an illustration showing the second layer containing a fat soluble anti-oxidant (flavonoids) surrounding the first layer containing MCC that surrounds the seed granule.
Figure 7:
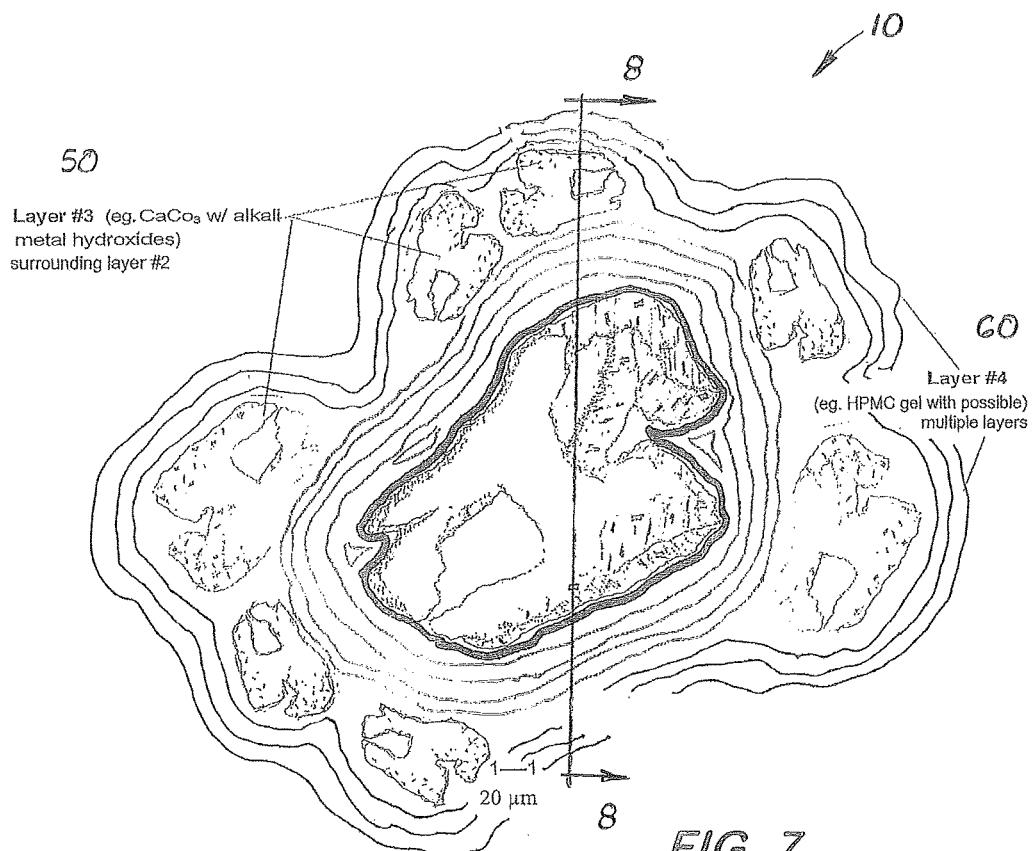
FIG. 7 is a sectional, side elevational view of the seed granule covered by the second and first layers shown in FIG. 6.
Figure 8:
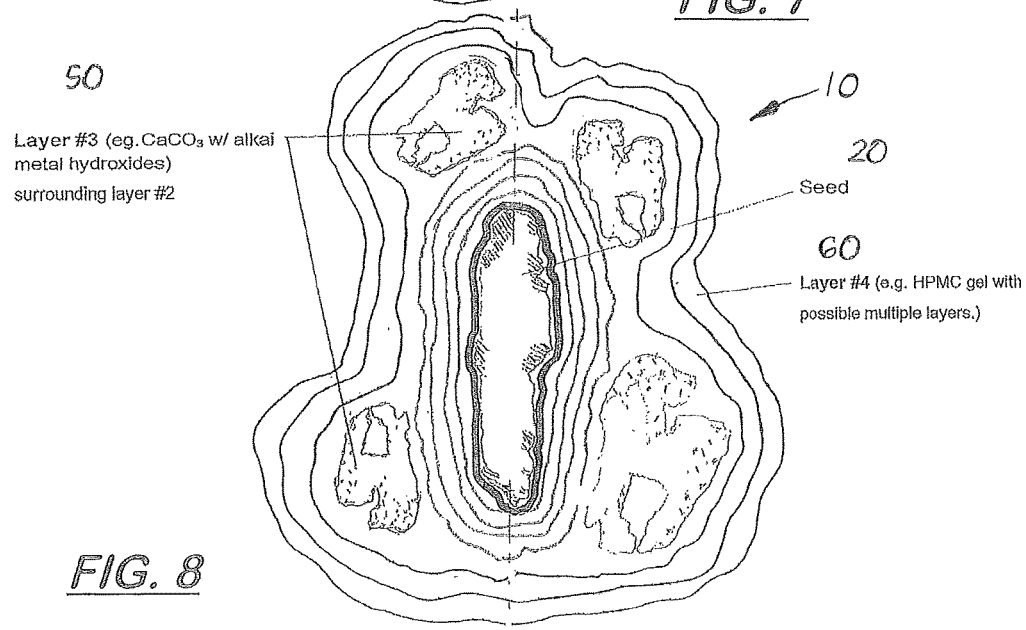
FIG. 8 is an illustration showing the third layer containing Type 1 granules of CaCO3 with alkali metal hydroxides surrounding the second layer containing a fat soluble anti-oxidant (flavonoids) that surrounds the first layer containing MCC and surrounds the seed granule.
Figure 9:
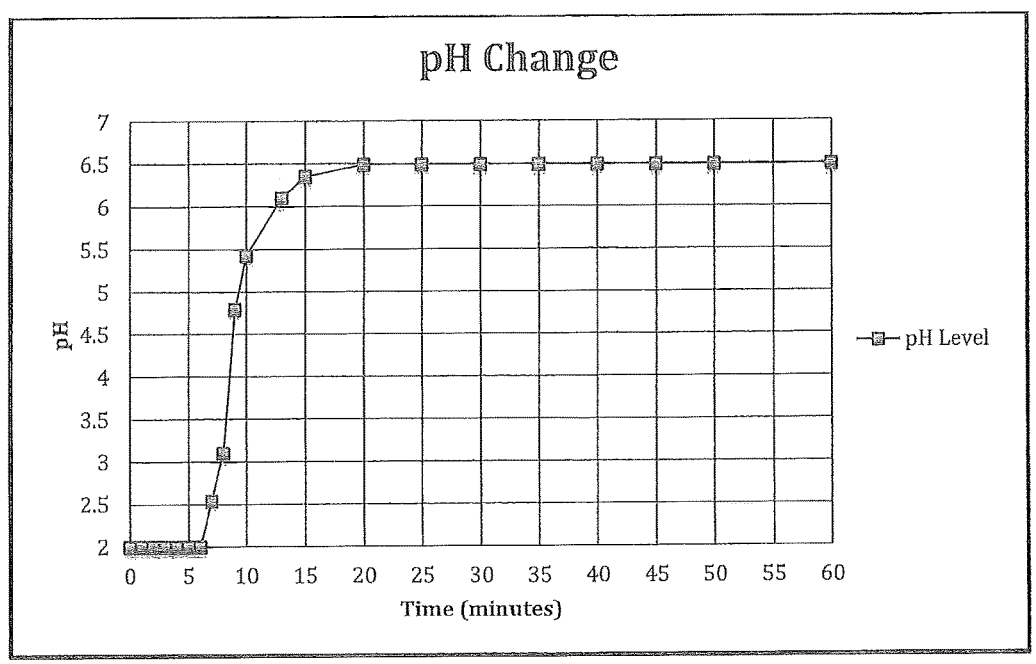
FIG. 9 is an illustration showing the fourth layer containing HPMC gel that surrounds the third layer containing CaCO3 with alkali metal hydroxide, an inner second layer containing a fat soluble anti-oxidant, and inner first layer containing MCC that surrounds the seed granule.
Figure 10:
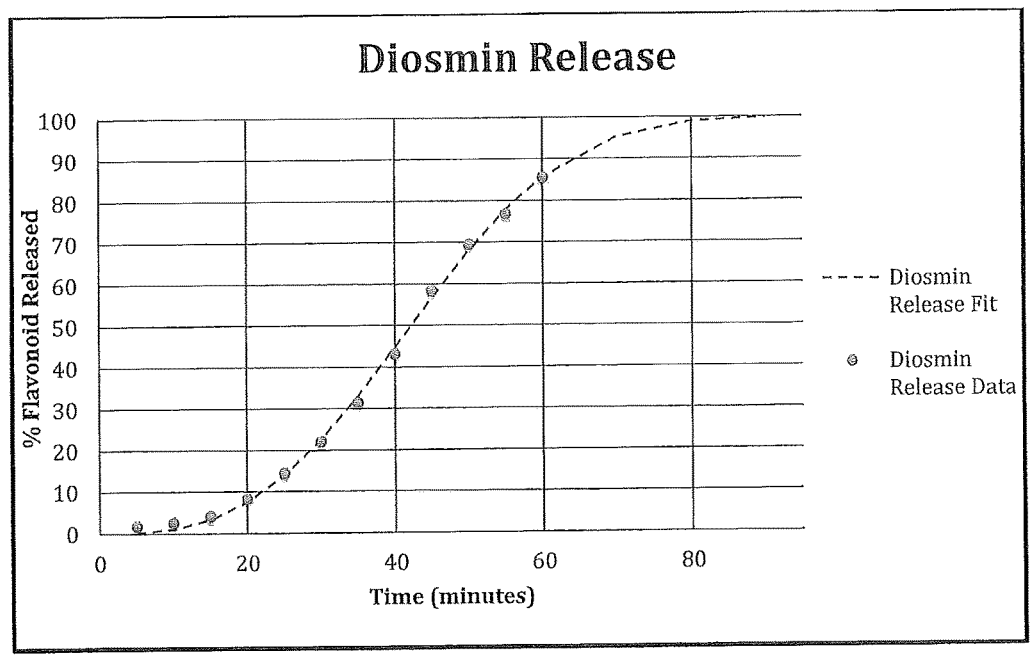
FIG. 10 is a graph showing the dissolution rate and acid neutralizing effect of layer 3 and layer 4 of a particle over time in 2.0 pH HCl to simulate stomach acid.
Figure 11:
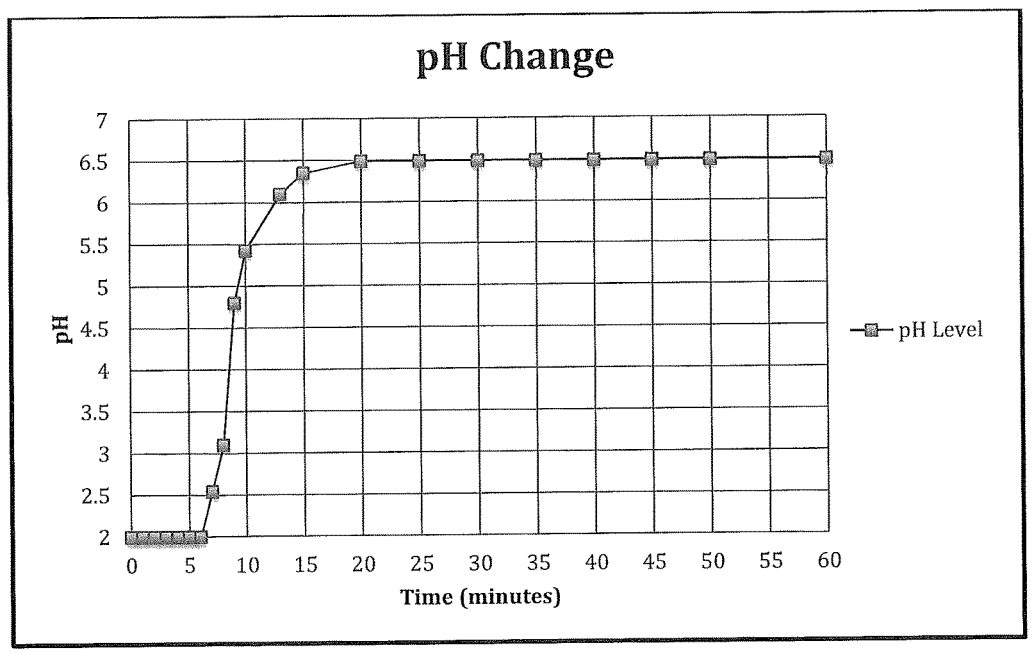
FIG. 11 is a graph showing the dissolution rate of Diosmin (a type of FSA) over time as it disperses and dissolves into solution after surviving 2.0 pH HCl for 20 minutes.

Unless defined otherwise, all technical and scientific terms used have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context dictates otherwise. For example, "the flavonoid" may refer to a mixture of several compatible flavonoids that comprise a component of the finished composition.

As used, "subject" or "individual" or "patient" refers to any subject for whom or which therapy is desired, and refers to the recipient of the therapy to be practiced according to the invention. The subject can be male or female.

As used, "fat soluble antioxidants" or "FSA" are phenolic or polyphenolic phytochemicals with low solubility in water and neutralize oxygen free radicals in vitro. They include vitamin E, ellagic acid, curcumin, capsaicin and the flavonoid family of compounds. Flavonoids are a class of plant metabolites with a general structure of a 15-carbon skeleton, which comprises two phenyl rings and a heterocyclic ring. Fat soluble antioxidants include phytonutrients having a general structure of a 14- to 30-carbon skeleton, which comprises two phenyl rings and their metabolites whether they be free or held in lipids, liposomes, albumins, cyclodextrin, cucurbituryl, surfactants, and polymers.

II. Sustained Release Fat Soluble Antioxidant Particles a. General Description:

The sustained release fat soluble antioxidant particles are composed of an inner seed granule surrounded by three (3) layers and at least one outer gel layer.

There are two types of particles: Type 1 and Type 2. A Type 1 particle is made of a plurality of seed granules each made of microscopic (0.5 μm to 20 μm) alkaline earth metal salt crystals (preferably calcium carbonate) containing fissures on the face of the crystal and agglomerated using microcrystalline cellulose ("MCC") and/or croscarmellose sodium. A Type 2 particle is a single seed granule made of single alkaline earth metal salt crystal (preferably calcium carbonate) containing microscopic fissures. Disposed in the interstitial space of Type 1 and in the microscopic fissures of Type 1 and Type 2 seed granule are microscopic particles of alkali metal salt, alkali metal hydroxide and/or other ions.

The first layer surrounds the seed granule and is made of pH neutral excipients that protect and shield the seed granule from the second layer containing a fat soluble antioxidant.

The fat soluble antioxidant material in the second layer is held in a polymer matrix and surrounds the first layer;

A third layer contains a fine mixture of microscopic alkaline earth metal crystals containing fissures and interstitial spaces. Inside the fissures and interstitial spaces are particles of alkali earth metal hydroxide held with pH neutral excipients in a polysaccharide or polymer gel. The selection and use of the polysaccharide or polymer gel holding the fine mixture of agglomerated alkaline earth metal crystals depends on the characteristics of the second layer fat soluble antioxidant.

One or more outer gel layers containing a thermal-sensitive polymer (preferably hydroxypropyl methylcellulose or HPMC) are heated sufficiently to form a protective gelation around the third layer to complete the coating process.

The resulting particles are sized with shape and surface area effective to permit easy pressing as tablets and filling in capsules, gel caps and other oral delivery systems typically no larger than 800 μm.

b. Granule Components:

Each seed granule is made of alkaline earth metal salt crystals (preferably calcium carbonate) with a low solubility in water and a high degree of fissuring on the face of the crystal. There are two types of seed granules: seed granules known as Type 1 seed granules are made of a plurality of microscopic seed granules crystals agglomerated and bound with microcrystalline cellulose (MCC) and croscarmellose sodium or a single granule crystal known as Type 2. Disposed within the fissures and interstitial space of the Type 1 seed granules or the fissures of the Type 2 seed granule are alkali metal salt crystals (such as potassium hydroxide, potassium chloride and sodium hydroxide) with high solubility in water plus other ionic molecules with similar characteristics that may assist in absorption in the GI tract. The components which easily ionized in water are mixed with the other components in a shear mixer extensively with appropriate diffused liquid so the alkali metal salts and similar molecules (typically in ionic form) reside within fissures and interstitial spaces of the seed granules.

The first layer surrounding the seed granule agglomerate or the single seed granule is made of one or more alkaline-resistant excipients that dissolve easily in an aqueous liquid medium but withstand high pH without degradation or reaction (like microcrystalline cellulose and croscarmellose sodium) and dried to 3% to 7% moisture content to seal in the highly reactive alkali metal salts in the seed granule.

The second layer is a mixture of fat soluble antioxidants. In the embodiment presented the fat soluble antioxidant is a flavonoid. The flavonoid is suspended in a non-reactive polysaccharide or a polymer gel and dried.

The third layer is made of microscopic (0.5 μm to 20 μm) alkaline earth metal salt crystals (preferably calcium carbonate) with low solubility in water and a plurality of fissures on the face of the alkaline earth metal salt crystals. The microscopic alkaline earth mineral salt crystals may be agglomerated to create interstitial spaces between the crystals. If agglomerated, the binding material will be microcrystalline cellulose (MCC) and/or croscarmellose sodium. Inside the fissures and interstitial spaces between the alkaline earth salt crystals are alkali metal salt crystals with high pH characteristics (preferably potassium hydroxide and/or sodium hydroxide) with high solubility in water. The third layer may also use a non-reactive poly saccharide or polymer gel as a binder to connect the third layer with the second layer depending on the second layer fat soluble antioxidant. The third layer is dried to 3% to 7% moisture content to seal in the highly reactive alkali metal salts.

One or more outer layers form an outer cover for the third layer and comprise one or more coatings with a thermal-sensitive polymer gel (typically preferably hydroxypropyl methylcellulose or HPMC) that is non-reactive with anti-oxidants and can withstand a wide range of pH levels without rapid deterioration.

The finished particle is sized to have a size, shape, and surface area effective to permit easy pressing as tablets and filling in capsules, gel caps and other oral delivery systems.

c. Size, Shape, Surface Area—Volume Ratio and/or Weight Ratio—for Various Layers that Comprise the Particle:

Seed granule agglomerate used in the Type 1 particle is made of a plurality of seed granules that measure approximately (0.5 μm to 20 μm) in size and made of alkaline earth metal salt crystals. When bounded, the seed granule agglomerate is irregularly shaped between 50 μm and 500 μm in the longest dimension. The single seed granule is also irregularly shaped between 100 μm and 500 μm in its longest dimension with a low solubility in water. The alkaline earth metal salt crystals are selected for the high surface area offered by fissures on the face of the crystals. Located inside the fissures of each single seed granule and inside the fissures and interstitial space of the seed granules used in the seed granules agglomerate are alkali metal salt crystals in ionic form (such as potassium hydroxide, potassium chloride and/or sodium hydroxide) with high solubility in water amounting to 3% to 7% of the seed granule's mass (exclusive of binders). Also inside the fissures of the single seed granule and the fissures and interstitial spaces of seed granule agglomerates may be other ionic molecules with similar physical characteristics that may assist in absorption in the GI tract amounting to 0% to 10% of the seed granule mass (exclusive of binders). The seed granule mass is between 10% to 20% of the finished particle mass.

The first layer comprises one or more alkaline-resistant excipients that dissolve easily in a aqueous liquid medium but withstand high pH without degradation or reaction (like microcrystalline cellulose and croscarmellose sodium) and dried to 3% to 7% moisture content and is up to 5 μm in thickness and comprises a negligible mass in the finished granule. The second layer comprising a mixture of fat soluble antioxidant material suspended in a non-reactive polysaccharide or a polymer gel is dried to form a layer of one or more fat soluble antioxidants in an unaltered condition 15 μm to 100 μm thick and equal to 100% to 300% of the volume of the seed granule and 15% to 40% of the finished particle mass.

The third layer is made of small (0.5 μm to 20 μm) alkaline earth metal salt crystals (preferably calcium carbonate) with a low solubility in water and significant fissuring on the face of the crystals. The alkaline earth metal crystals equal 90% to 95% of the layer #3 mass (exclusive of binders). The balance of the third layer mass (exclusive of binders) are alkali metal salt crystals with high pH characteristics (preferably potassium hydroxide and sodium hydroxide). Sufficient diffused water is mixed with the alkali metal salt crystals and the alkaline earth metal crystals so the alkali metal salt crystals (typically in ionic form) reside within fissures of the alkali earth metal salt crystals and are bound with one or more alkaline-resistant excipients that dissolve easily in a aqueous liquid medium but withstand high pH without degradation or reaction (like microcrystalline cellulose and croscarmellose sodium). The third layer is dried to 3% to 7% moisture content so the third layer surrounds the second layer with a covering 20 μm to 200 μm thick and may comprise 15% to 30% of the mass of the finished particle.

The fourth layer comprises one or more coatings with a thermo-sensitive polymer gel (typically preferably hydroxypropyl methylcellulose) that is non-reactive with anti-oxidants and can withstand a wide range of pH levels without rapid deterioration that is between 50 μm and 100 μm thick and may comprise 20% to 35% of the mass of the finished particle.

The resulting particle is finished by sizing through shear mixers in a partial vacuum to have a size, shape, and surface area effective to permit easy pressing as tablets and filling in capsules, gel caps and other oral delivery systems that is no larger than 800 μm in diameter.

d. Method of Manufacture:

Seed granule and the first layer are manufactured in an apparatus designed for damp agglomeration and rapid drying of particulate material. The apparatus comprises an agglomerator for mixing and forming, over a period of several hours, the requisite materials with diffuse water to form a damp granular material, discharging the damp granular material (less than 40% moisture content) through a rotary blade assembly that repeatedly impacts and cuts the mixture to be agglomerated which is forced out radially through the blade assembly under centrifugal and vacuum pressure toward an annular screen. When the damp granules meet a predetermined size or smaller, they move into a dryer apparatus with baffle defining a spiral path through which the granule exits dry with a carefully adjusted moisture content. This process is referred to as "damp agglomeration." The seed granule and first layer are manufactured together in the damp agglomeration apparatus under ambient temperature so the damp granule enters the rotary blade assembly with a moisture content less than 25%. The first layer is applied at the later stage of the mixing process at the same moisture content as the damp granules. The first layer integrates with the seed granule as it is forced through the blade assembly under centrifugal and vacuum pressure toward an annular screen and dried. The selection of a Type 1 or Type 2 seed granule depends on fat soluble antioxidant ("FSA") and reactive characteristics of the FSA.

One method of applying the second layer (containing the fat soluble antioxidant mixture) is to add the mixture to the last stage of the damp agglomeration process so it enters with less than 20% moisture content and is processed through the damp agglomeration apparatus with the seed and first layer to exit the damp agglomerator with between 5% and 10% moisture content.

In the alternative, the second layer may be applied over the dried seed granule with the first layer using a fluid bed coating apparatus operating in an inert gas atmosphere if the fat soluble antioxidant ROS characteristics indicate a need for such care. The fat soluble antioxidant is suspended in a non-reactive polysaccharide or polymer gel and sprayed into a stream of seed granules with the first layer already applied. The fat soluble antioxidant coating is immediately dried in the hot gas stream. The spray system may use a sonic vibration technique or other micro-droplet generating system and a continuous recycling process to regulate the thickness of the second layer to complete the application of the second layer.

The third layer is applied using two steps. The first step uses the same procedure and damp agglomeration apparatus as the Type 1 seed granule to produce super fine alkaline earth metal granules with alkali metal hydroxides dispersed within fissures and interstitial spaces having a finished moisture content of less than 15%. The second step in applying the third layer is accomplished with a fluid bed coating apparatus in which Type 1 granules are suspended in a poly saccharide or polymer gel to be spray dried on particles containing the seed, first and second layers. If the fat soluble antioxidant ROS characteristics indicate special care in needed, the process will be done in an inert gas atmosphere.

The outer layer may be applied to the third layer by adding a thermal-sensitive polymer gel to be spray dried on particles containing the seed, first, second and third layers then heated to harden the thermal-sensitive polymer. The third layer and outer layer may be applied in one procedure in which a mixture of super fine Type 1 granules are mixed with a thermo-sensitive polymer gel and spray dried on particles containing the seed, first and second layers and heated in the spray dry apparatus to harden the thermal-sensitive polymer. Finished particles are sifted and any particles not passing through a #80 U.S.A. Standard Testing Sieve will be fed through a rotary blade assembly that repeatedly impacts and cuts the mixture forced out radially through the blade assembly under centrifugal and vacuum pressure toward an annular screen when the particles meet a predetermined size or smaller and into a dryer apparatus if necessary to get meet moisture content requirements for size, shape, and surface area effective to permit easy pressing as tablets and filling in capsules, gel caps and other oral delivery systems. An outer coat may be reapplied to the sized particles if significant fracturing occurs during the final sixing step in manufacturing process.

e. Method(s) of Use:

a. The resulting four layer particles are stored in air and moisture proof containers to be shipped to packaging facilities to be pressed into tablets or filled into capsules and bottled for use as dietary supplements or medical foods. The air and moisture proof containers are shipped to packaging facilities to fill air and moisture proof packets for use as food additives to be mixed with food or drink prior to consumption.

b. One embodiment of the invention is a four-layer particle comprising the flavonoid diosmin that would pressed into a tablet or filled into a capsule for daily ingestion as a method to alleviate chronic venous insufficiency or loaded into a water and air proof packet suitable for adding to water or food and ingested daily as a method to alleviate chronic venous insufficiency.

c. Another embodiment of the invention is a four-layer particle comprising the flavonoid cyanidin that would be pressed into a tablet or filled into a capsule for daily ingestion as a method to inhibit development of diabetes and/or obesity and loaded into a water and air proof packet suitable for adding to water or food and ingested daily as a method to inhibit development of diabetes and/or obesity.

In compliance with the statute, the invention described has been described in language more or less specific on structural features. It should be understood however, that the invention is not limited to the specific features shown, since the means and construction shown, comprises the preferred embodiments for putting the invention into effect. The invention is therefore claimed in its forms or modifications within the legitimate and valid scope of the amended claims, appropriately interpreted under the doctrine of equivalents.

We claim:

1. An oral formulation for the controlled release of fat soluble antioxidants made up of particles, each particle comprising;
   a. seed granules each made of calcium carbonate with microscopic fissures and interstitial spaces formed therein, disposed inside said microscopic fissures and said interstitial spaces are microscopic particles made of alkali metal salt, or alkali metal hydroxide;
   b. a first layer made of microcrystalline cellulose and croscarmellose sodium surrounding said seed granules;
   c. a second layer comprising a mixture of a fat soluble antioxidant and a polysaccharide or polypeptide binder or a polymer gel;
   d. a third layer surrounding said second layer, said third layer made of microscopic alkaline earth metal salt particles mixed with an alkali metal hydroxide, microcrystalline cellulose, croscarmellose sodium binders, and a polysaccharide gel or a polymer gel; and,
   e. at least one outer gel layer surrounding said third layer.

2. The oral formulation, as recited in claim 1, wherein each said seed granule is 100 μm to 500 μm in diameter.

3. The oral formulation, as recited in claim 1, wherein said micro particles are 7% to 10% by weight of said seed granule.

4. The oral formulation, as recited in claim 1, wherein said second layer is 15 μm to 100 μm thick.

5. The oral formulation, as recited in claim 2, wherein said second layer is 15 μm to 100 μm thick.

6. The oral formulation, as recited in claim 1, wherein said third layer is made of calcium carbonate.

7. The oral formulation, as recited in claim 1, wherein said outer gel layer is made of hydroxypropyl methylcellulose.

8. The oral formulation, as recited in claim 1, wherein said seed granules are bound to at least one adjacent seed granule and said interstitial spaces are formed between.

9. The oral formulation, as recited in claim 8, further including said alkali metal salt crystals located in said interstitial spaces.

* * * * *